United States Patent [19]
Walker et al.

[11] 3,940,432
[45] Feb. 24, 1976

[54] PROCESS FOR MAKING ETHYLENE GLYCOL

[75] Inventors: Wellington E. Walker, Charleston; Jean B. Cropley, South Charleston, both of W. Va.

[73] Assignee: Union Carbide Corporation, New York, N.Y.

[22] Filed: May 15, 1974

[21] Appl. No.: 470,115

Related U.S. Application Data

[63] Continuation-in-part of Ser. No. 371,353, June 19, 1973, abandoned.

[52] U.S. Cl...... 260/449 R; 252/431 R; 252/431 N; 252/443; 260/449 L; 260/449.5
[51] Int. Cl.$^2$.................... C07C 27/06; C07C 29/16
[58] Field of Search......... 260/449 R, 449 L, 449.5, 260/449.6; 252/431 R, 431 N, 443

[56] References Cited
UNITED STATES PATENTS

| | | | |
|---|---|---|---|
| 1,741,307 | 12/1929 | Jaeger............................... | 260/449 R |
| 2,534,018 | 12/1950 | Gresham........................... | 260/449.6 |
| 2,636,046 | 4/1953 | Gresham........................... | 260/449.6 |
| 3,081,357 | 3/1963 | Alderson et al. ................... | 260/435 |
| 3,351,666 | 11/1967 | Mertzweiller et al........... | 252/431 R |
| 3,644,446 | 2/1972 | Booth et al. ......................... | 252/431 |
| 3,833,634 | 6/1974 | Pruett et al. ..................... | 260/449 R |

FOREIGN PATENTS OR APPLICATIONS

| | | | |
|---|---|---|---|
| 655,237 | 7/1951 | United Kingdom.......... | 260/449.6 R |

*Primary Examiner*—Howard T. Mars
*Attorney, Agent, or Firm*—George A. Skoler

[57] ABSTRACT

This invention is concerned with improving the ethylene glycol production capabilities of the metal carbonyl catalyzed reaction between carbon monoxide and hydrogen by conducting the reaction such that the ethylene glycol concentration in the reaction mixture is less than 5 gram moles per liter, preferably between about 0.4 to 5 gram moles per liter of reaction mixture and the molar formation ratio between ethylene glycol and methanol in the reaction mixture exceeds about 0.3. In a preferred embodiment, a continuous process is operated in such a manner that the concentration of ethylene glycol in the product mixture removed from the reactor is greater than the average concentration of ethylene glycol in the reactor.

7 Claims, 1 Drawing Figure

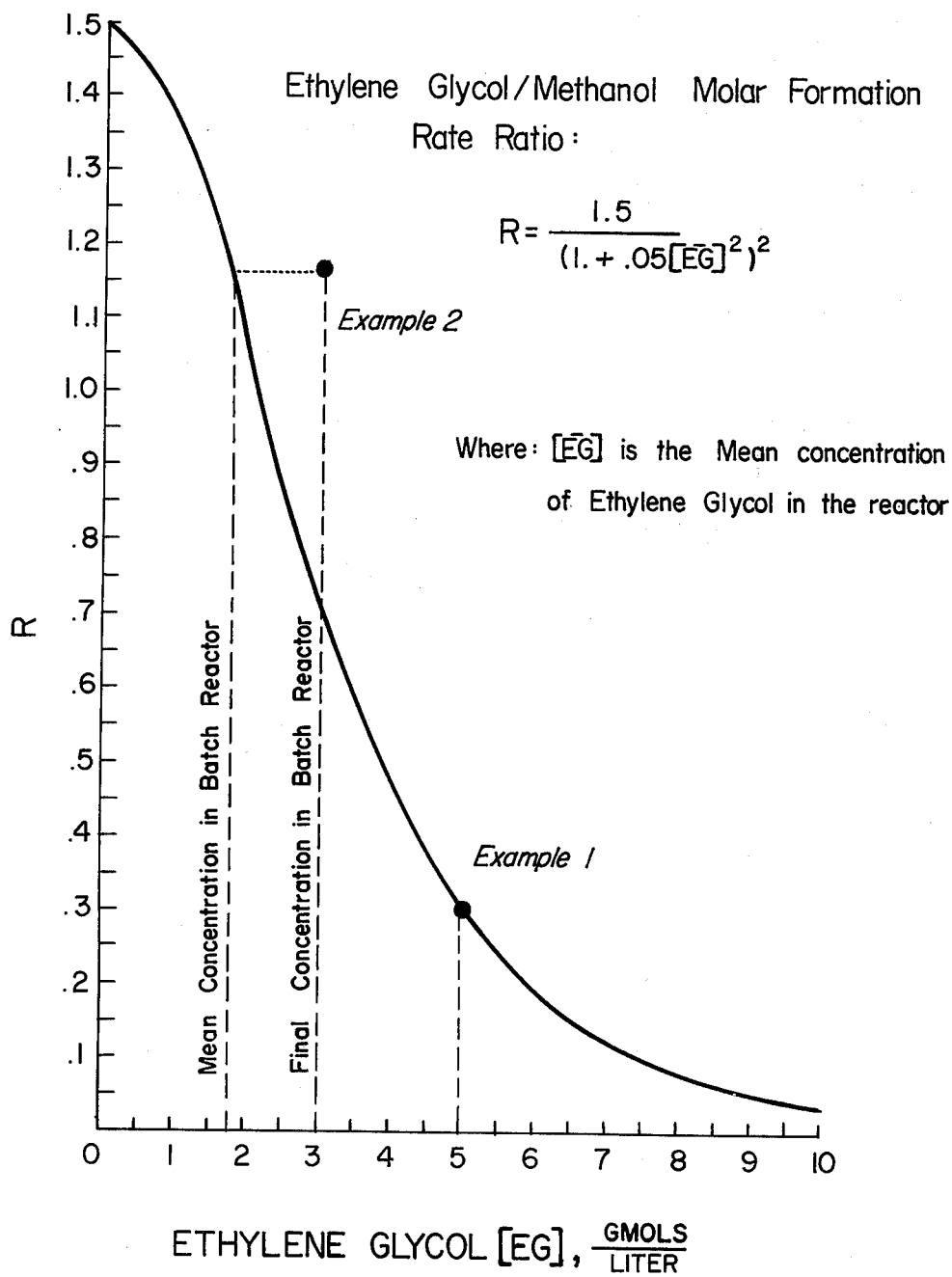

PROCESS FOR MAKING ETHYLENE GLYCOL

This application is a continuation-in-part of copending application, Ser. No. 371,353, filed June 19, 1973 and now abandoned.

This invention is concerned with the effective production of ethylene glycol and methanol from the reaction between carbon monoxide and hydrogen in the presence of a metal carbonyl catalyst at elevated pressures and temperatures.

There are described in copending applications Ser. No. 219,130, filed Jan. 19, 1972, now U.S. Pat. No. 3,833,634, patented Sept. 3, 1974; and Ser. No. 371,350, filed on even date herewith, rhodium carbonyl catalyzed reactions between carbon monoxide and hydrogen to produce methanol and ethylene glycol as primary products. British Patent Specification 655,237, U.S. Pat. Nos. 2,534,018; 2,570,792; and 2,636,046, mention the use of cobalt carbonyl compounds and carbonyl compounds of nickel, copper, chromium, and manganese as catalysts in the formation of ethylene glycol from the reaction of carbon monoxide and hydrogen.

It is the purpose of this invention to define an improvement in the operation of said metal carbonyl catalyzed reactions so as to maximize the production of the more valued ethylene glycol.

It has been surprisingly found that at the earliest stages of reaction in the aforementioned metal catalyzed carbonyl reactions between carbon monoxide and hydrogen, ethylene glycol is produced at a faster rate than methanol. Moreover, it has also been surprisingly found that simultaneous with an increased concentration of ethylene glycol in the reaction mixture there occurs a concomitant decrease in its rate of formation and an increase in the rate of methanol formation. This means that if the most valued product of the reaction is ethylene glycol, one must control its concentration in the reaction mixture to insure economically acceptable ethylene glycol efficiencies and production rates.

This invention is concerned with an improvement in the processes of said patents and said copending patent applications. This improvement involves operating said elevated pressure and temperature reactions with certain limits on the build-up of ethylene glycol in the reaction mixture. The result of such operation of the process is enhancement in both the rate of ethylene glycol efficiencies and ethylene glycol production.

Therefore, it has been determined that if such metal carbonyl catalyzed reactions between carbon monoxide and hydrogen are conducted such that the ethylene glycol concentration in the reaction mixture is less than about 5 gram moles per liter, preferably between 0.4 and 5 gram moles per liter of reaction mixture and the molar formation ratio between ethylene glycol and methanol in the reaction mixture exceeds about 0.3, the production recovery and efficiency, and the production rate of ethylene glycol is significantly better, to thereby enhance the possible use of such processes in the commercial manufacture of ethylene glycol.

Reference is made to the FIGURE which graphically portrays the relationship and effect of the molar concentration of ethylene glycol on the mole ratio of ethylene glycol to methanol in the reaction mixture.

The determination of the mole rate of formation of ethylene glycol or methanol, as shown in the FIGURE, is independent of time. At the beginning of the reaction, using a rhodium carbonyl catalyst at 210°C and 20,000 psia pressure of a 1:1 molar mixture of CO and $H_2$, the reaction favors ethylene glycol formation but as the reaction continues, methanol formation is favored. However, if the concentration of ethylene glycol in the produced reaction mixture is reduced, after a period of reaction, the rate of its formation will be materially improved with a consequent reduction in methanol formation.

The following examples 1 and 2 characterize the effect of mode of operating a high pressure reactor to demonstrate the principle discussed above as it would be seen if the reactor were a batch reactor, as shown in Example 1, which also relates the principles of a continuous reactor where the final product's ethylene glycol concentration is greater than the average ethylene glycol concentration in the reactor. The principles of a continuous back mix type reactor are shown in Example 2 where the final product's ethylene glycol concentration is the same as the average concentration in the reactor.

EXAMPLE 1

The reactor for this example is a heavy-wall stainless steel autoclave fitted with a magnetic drive stirrer comprising two turbines located at roughly the midpoint of the vessel and three inches from the bottom head, respectively, and surrounded by a combination draft-tube and cooling coil to remove the heat of reaction and to provide for adequate mixing of the gas/liquid mixture. Several ports are available in both bottom and top heads through which reactants may be added and products removed. The interior cavity of the autoclave is 16 inches long by 7.65 inches in internal diameter, the overall volume being roughly 12.0 liters. The reactor is fitted with an external jacket through which temperature controlled hot oil is fed in addition to the oil fed to the cooling coil.

An initial charge of 3000 grams of tetraglyme containing 3000 ppm of rhodim as the catalyst, formed by reacting 4 moles of 2-hydroxypyridine and 1 mole of rhodium dicarbonyl acetylacetonate, is introduced to the reactor, and synthesis gas having a composition of 60 percent hydrogen and 40 percent carbon monoxide is introduced to the reactor, thereby raising its pressure to the reaction pressure of 20,000 psi. Throughout the duration of the reaction the pressure is maintained at 20,000 psi by the addition of additional synthesis gas as required. Reaction temperature is maintained at 220°C by adjusting temperature of hot oil fed to the jacket and coil.

At the end of four hours, the reactor is cooled to ambient conditions, the pressure vented, and liquid products recovered. They are primarily 360 grams of methanol and 816 grams of ethylene glycol, together with the 3000 grams of tetraglyme originally charged. Approximately 204 grams of other miscellaneous chemicals are also recovered. The concentrations of ethylene glycol and methanol in the liquid product are thus seen to be 3.00 and 2.57 gmol/liter, respectively, and the molar formation rate ratio is seen to be 13.16 gmols of ethylene glycol to 11.25 gmols of methanol, or 1.17:1.

EXAMPLE 2

The reactor of example 1 is utilized in this experiment, with liquid and gas being continuously fed and withdrawn from the reactor. The reaction temperature and pressure are the same as in example 1, i.e., 20,000 psi and 220°C.

Synthesis gas having a composition of 60 percent hydrogen and 40 percent carbon monoxide is fed to the reactor at a rate of about 50 standard cubic feet per hour and tetraglyme solvent containing 2.0 wt. percent of rhodium, as the rhodium catalyst of example 1, is fed in the amount of 100 grams, per hour.

Liquid and gaseous products are withdrawn continuously from the reactor as required to maintain reaction pressure, the two phases being removed as a froth and separated at lower pressure downstream of the reactor.

The steady-state liquid product withdrawal rate is 636 grams per hour, which contains 197 grams of ethylene glycol (3.18 gmol) at a concentration of 5 gmol/liter and 340 grams methanol (10.62 gmol) at a concentration of 16.7 gmol/liter.

The molar formation rate ratio is seen to be 3.18 gmol of ethylene glycol for 10.62 gmol of methanol, or a ratio of 0.3 to 1. In the above examples, "tetraglyme" is the dimethyl ether of tetraethylene glycol.

In comparing the results of experiments cited in example 1 and 2 with the curve of the FIGURE, it is important to recognize two fundamental influences on the course of the reaction. These fundamental influences are the concentration of ethylene glycol in the liquid product, and the effect of the reactor geometry and or mode of operation upon its performance. In particular is to be noted the results of Example 2, in which a continuous back-mixed reactor is operated in such a way that the product concentration (and, therefore, the average concentration) of ethylene glycol was 5.0 gmol/liter. This level of ethylene glycol concentration caused the molar formation rate ratio of ethylene glycol to methanol to be 0.3:1, in accordance with the graph of the FIGURE.

Conversely, the batch reactor of Example 1, while producing a final product concentration of 3.0 grammols ethylene glycol/liter, nevertheless operated at an effectively lower ethylene glycol concentration, because there was no ethylene glycol at all in the reactor at the beginning of the experiment. Thus the effective concentration of ethylene glycol is seen to be considerably less than the 3.0 final concentration, and the molar formation rate ratio is seen to be not 0.71, as predicted from the graph of the FIGURE, but 1.17:1, which would correspond to an effective concentration on the graph of about 1.6 gmol/liter, an entirely reasonable average number.

An important embodiment of this invention, one which provides optimum production of ethylene glycol, is to practice this process such that the concentration of ethylene glycol in the products withdrawn from the reactor is greater than the average concentration of ethylene glycol in the reactor. In a continuous process, this is easily effected in a tubular or plug flow reactor where the reactants are introduced at one end of the reactor and withdrawn from the other in the absence of significant back mixing. This same embodiment can be practiced with a plurality of back mix reactors interconnected in series. Five to ten of such back mix reactor in series simulate the effect of a plug flow reactor.

In more specific terms, this process involves the reaction of carbon monoxide and hydrogen in the presence of metal carbonyl compounds, as aforedefined, and particularly rhodium carbonyl clusters which possess an infrared spectrum which exhibits three intense wavelength bands between about plus and minus 10 $cm^{-1}$ of about 1868 $cm^{-1}$, about 1838 $cm^{-1}$, and about 1785 $cm^{-1}$ at a pressure of at least about 500 pounds per square inch absolute (psia), as set forth in copending application Ser. No. 371,350.

P. Chini, in a review article entitled "The Closed Metal Carbonyl Clusters" published in Reviews (1968), Inorganica Chimica Acta, pages 31–50, states that a metal cluster compound is "a finite group of metal atoms which are held together entirely, mainly, or at least to a significant extent, by bonds directly between the metal atoms even though some non-metal atoms may be associated intimately with the cluster." The rhodium carbonyl cluster compounds contain rhodium bonded to rhodium or rhodium bonded to another metal, such as cobalt and/or iridium. The preferable rhodium carbonyl cluster compounds are those which contain rhodium-rhodium bonds. These compounds desirably contain carbon and oxygen in the form of carbonyl (—C—O), in which the carbonyl may be "terminal", "edge bridging" and/or "face bridging". They may also contain hydrogen and carbon in forms other than carbonyl. The following are structures of two useable rhodium carbonyl cluster ions:

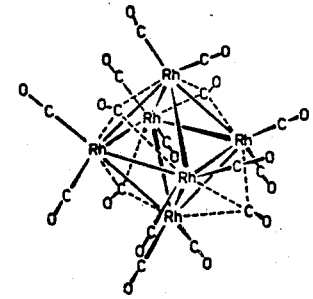

$Rh_6(CO)_{16}$

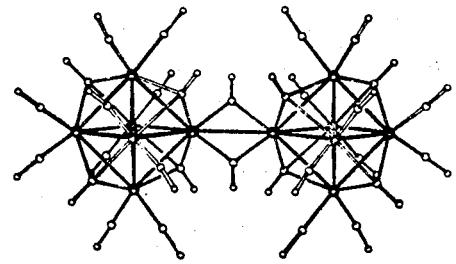

$[Rh_{12}(CO)_{30}]^{2-}$

Rhodium carbonyl cluster ions which possess the infrared spectrum characterized previously, function in association with carbon monoxide and hydrogen, as herein defined, to produce the polyhydric alcohols etc. The exact mechanism by which the cluster compounds act to catalyze the reaction is not fully appreciated at this time. It is believed that the reaction is dependent upon the existance of the following equilibria:

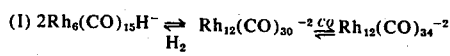

(I) $2Rh_6(CO)_{15}H^- \rightleftharpoons Rh_{12}(CO)_{30}^{-2} \rightleftharpoons Rh_{12}(CO)_{34}^{-2}$
$H_2$ The clusters are ionic and they can be associated with any counter-ion provided that conditions are available by which a rhodium carbonyl cluster compound having aforedefined infrared spectrum characteristics is obtainable.

The counter-ion may be rhodium per se, hydrogen, ammonia, any monovalent or polyvalent metal, and a broad range of organic compounds, such as those characterized as ligands.

The monovalent or polyvalent metal counter-ion may include lithium, sodium, potassium, rubidium, cesium, francium, beryllium, magnesium, calcium, strontium, barium, radium, scandium, yttrium, the rare earth metals (especially, e.g., cerium, praseodymium, and europium), titanium, zirconium, hafnium, manganese, rhenium, iron, ruthenium, osmium, cobalt, rhodium, iridium, nickel, palladium, platinum, copper, silver, gold, boron, aluminum, gallium, indium and thallium.

The organic counter-ions may result from "complexing" organic compounds with the rhodium carbonyl cluster ions or by ionically associating with the cluster.

The term "complex" means a coordination compound formed by the union of one or more electronically rich molecules or atoms capable of independent existence with one or more electronically poor molecules or atoms, each of which is also capable of independent existence. These organic rhodium cluster complexes are derived from the association of organic ligands with rhodium carbonyl solutions.

Organic ligands which are suitable in the practice of the invention contain at least one nitrogen atom (hereinafter called Lewis base nitrogen atom) and/or at least one oxygen atom (hereafter called Lewis base oxygen atom), said atoms possessing a pair of electrons available for the formation of coordinate bonds with rhodium. Desirably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with rhodium, and said organic ligand forming with rhodium per se a chelate structure. In suitable embodiments the organic ligands contain from 2 and upwards to 4 Lewis base atoms, preferably from 2 to 3 such atoms, and most preferably 2 Lewis base atoms. These organic ligands are said to be multidentate or polydentate, that is to say, such ligands are bidentate, tridentate, or quadridentate, depending on whether 2, 3, or 4 Lewis base atoms are involved in the formations of chelate structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino

nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the $$-\overset{O}{\underset{\|}{C}}OH$$

group and the "oxy" oxygen in the

group that are the Lewis base atoms. The organic ligands may also contain other atoms and/or groups such as alkyl, cycloalkyl, aryl, chloro, ,thiaalkyl, trialkylsilyl, and the like.

Illustrative organic nitrogen ligands include for instance, N,N,N',N'-tetramethylethylenediamene, N,N,N',N'-tetraethylethylenediamine, N,N,N',N'-tetra-n-propylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine, 2,2'-dipyridyl, methyl-substituted 2,2'-dipyridyl, ethyl-substituted 2,2'-dipyridyl, 1,4-diazabicyclo [2.2.2] octane, methyl-substituted, 1,4-diazebicyclo [2.2.2] octane, purine, 2-aminopyridine, 2-(dimethylamino)pyridine, 1,10-phenanthroline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, and the like.

Illustrative organic oxygen ligands include, by way of illustrations, glycolic acid, methoxyacetic acid, ethoxyacetic acid, diglycolic acid, thiodiglycolic acid, diether ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrolotriacetic acid, 2,5-dicarboxypiperazine, N-(2-hydroxyethyl)iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

In the practice of the invention a normally-liquid organic diluent is employed. Such diluents can be inert organic diluents, or they may be reactive diluents, and they can include the aforedescribed organic ligands, or mixtures thereof. Illustrative of the normally-liquid organic diluents which are generally suitable in the practice of desirable embodiments of the invention include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of ethylene glycol, of propylene glycol, of butylene glycol, of diethylene glycol, of dipropylene glycol, of triethylene glycol, of tetraethylene glycol, of dibutylene glycol, of oxyethyleneoxypropylene glycol, etc.; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethylhexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; anhydrides such as phthalic anhydride, acetic anhydride, etc.; and others. Tetrahydrofuran, dioxane, and the mono and dialkylethers of triethylene and tetraethylene glycol are preferred diluents. It should be noted that the use of reactive diluents in the practice of desirable embodiments of the invention can give rise to a range of useful products. For instance, the mono- and diacetate esters of ethylene glycol can be obtained by using acetate acid as the diluent in the reaction medium. The use of alkanols, e.g., methanol and ethanol, can result in the monoalkyl ethers of ethylene glycol.

The quantity of catalyst employed is not narrowly critical and can vary over a wide range and that cited in the aforementioned patents may be used. In general, the process is desirably conducted in the presence of a catalytically effective quantity of the active metal species, preferably the rhodium species, which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about 30 weight percent rhodium, and higher, and the realistic upper limit in practicing the invention appears to be dictated and controlled more by economics in view of the exceedingly high cost of rhodium metal and rhodium compounds. No particular advantages at the relatively high concentrations of rhodium are manifest. Depending on various factors such as the counter-ion of choice, the partial pressures of oxides of carbon and hydrogen, the total operative pressure of the system, the operative temperature, the choice of the normally-liquid organic diluent, and other considerations, a catalyst concentration of from about $1 \times 10^{-5}$ to about $1 \times 10^{-1}$ weight percent rhodium (contained in the catalyst) based on the total weight of reaction mixture, is generally desirable in the practice of the invention.

The operative temperature which may be employed can vary over a wide range of elevated temperatures. In general, the novel process can be conducted at a temperature in the range of from about 100°C. and upwards to approximately 375°C, and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

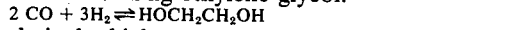

$$2\ CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150°C. to about 300°C., and desirably from about 190°C. to about 275°C.

The process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto which offset the unattractive plant investment outlay required for such high pressure equipment. In one embodiment of the invention, the upper pressure limitation is approximately 25,000 psia. Effecting the novel process below about 14,000 psia, especially below about 6,000 psia, results in cost advantages which are associated with low pressure equipment requirements. A suitable pressure range is from about 1000 psia to about 12,000 psia. The pressures referred to above represent the total pressure of hydrogen and oxides of carbon. In a preferred embodiment of the invention, rhodium catalyst is maintained in solution in the liquid reaction medium.

The novel process is effected for a period of time sufficient to produce the desired polyfunctional oxygen-containing products and/or derivatives thereof. In general, the residence can vary from minutes to several hours, e.g., from a few minutes to approximately 24 hours, and longer. It is readily appreciated that the residence period will be influenced to a significant extent by the effect of ethylene glycol buildup, by the reaction temperature, the concentration and choice of the catalyst, the total gas pressure and the partial pressure exerted by its components, the concentration and choice of diluent, and other factors. The synthesis of the desired product(s) by the reaction of hydrogen with carbon monoxide is suitably conducted under operative conditions which give reasonable reaction rates and/or conversions.

The relative amounts of carbon monoxide and hydrogen which are essentially present in the reaction mixture can be varied over a wide range. In general, the mol ratio of CO:H is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. Mixtures of carbon dioxide, carbon monoxide and hydrogen can also be employed. If desired, the reaction mixture can comprise steam and carbon monoxide.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As discussed previously, the operative conditions can be adjusted by control of ethylene glycol concentration to optimize the conversion of the desired product and/or the economics of the novel process. In a continuous process, for instance, when it is preferred to operate at relatively low conversions, it is generally desirable to recirculate unreacted synthesis gas with/without make-up carbon monoxide and hydrogen to the reactor. Recovery of the desired product can be achieved by methods well known in the art such as by distillation, fractionation, extraction, and the like. A fraction comprising rhodium catalyst, generally contained in by-products and/or normally-liquid organic diluent, can be recycled to the reaction zone, if desired. All or a portion of such fraction can be removed for recovery of the rhodium values or regeneration to the active rhodium species, if necessary. Fresh catalyst can be intermittently added to the recycle stream or directly to the reaction zone.

In preferred process, rhodium and other metal catalysts as defined herein which are soluble in the reaction medium have provided the best results.

The active forms of e.g., the rhodium carbonyl clusters may be prepared by various techniques. They can be preformed and then introduced into the reaction zone. Alternatively, any of the host of rhodium-containing substances as well as the counter-ion forming substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$). rhodium(II) formate, rhodium(II) acetate, rhodium(II) propionate, rhodium(II) butyrate, rhodium(II) valerate, rhodium(III) naphthenate, rhodium dicarbonyl acetylacetonate, rhodium tris(acetylacetonate), rhodium trihydroxide, indenylrhodium dicarbonyl, rhodium dicarbonyl (1-phenylbutane-1,3-dione), tris(hexane-2,4-dionato) rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), finely divided rhodium metal, rhodium metal and rhodium-containing compounds deposited on porous supports or carriers such as those exemplified previously, and others. The preparation of rhodium carbonyl cluster compounds is conveniently carried out in a diluent or mixture of diluents, e.g., benzene. Tetrarhodium dodecacarbonyl, though of limited solubility, can be added to the diluent in a finely divided form. Any of several of the rhodium-containing compounds illustrated previously can be employed in lieu of $Rh_4(CO)_{12}$. Organic ligands such as 2-hydroxypyridine or other counter-ion forming compounds can also be added thereto. The cluster forming reaction can be effected under a carbon monoxide pressure, with or without $H_2$, of about 1 to about 15 atmospheres, and higher, using a temperature of about 30°C. to about 100°C., for a period of time ranging from minutes to a few days, generally from about 30 minutes to about 24 hours. The resulting rhodium cluster compound contained in the organic diluent is catalytically active in this process. The compound contains rhodium in clustered combination with carbon monoxide and the counter-ion of choice. In preparing the aforesaid compounds, one can suitably employ from about 0.01 to about 20 moles of counter-ion forming compounds per mole of rhodium (contained in the rhodium compound used as a rhodium source). Ratios outside this stated range can be employed especially when it is desirable to use diluent quantities of the counter-ion forming compounds.

What is claimed is:

1. In the continuous process of producing ethylene glycol and methanol which comprises converting a mixture of a continuous feed of carbon monoxide and a continuous feed of hydrogen to produce ethylene glycol and methanol by contacting said mixture with a catalytic amount of rhodium in complex combination with carbon monoxide, at a temperature of between about 100°C. to about 375°C. and a pressure of between about 500 p.s.i.a. and about 50,000 p.s.i.a. sufficient to form said ethylene glycol and methanol, wherein the improvement comprises maintaining the concentration of ethylene glycol in the reaction mixture at less than about 5 gram moles per liter of reaction mixture from said reaction and maintaining the molar formation ratio between ethylene glycol and methanol in the reaction mixture in excess of about 0.3.

2. The process of claim 1 wherein the concentration of ethylene glycol in the product recovered from the reaction is greater than the average concentration of ethylene glycol in the reaction mixture prior to recovery.

3. The process of claim 1 wherein the rhodium in complex combination with carbon monoxide is in the form of a ionic rhodium carbonyl cluster compound.

4. The process of claim 3 wherein the temperature is between about 190°C. to about 275°C.

5. The process of claim 4 wherein the pressure is below about 14,000 p.s.i.a. and greater than about 1,000 p.s.i.a.

6. The process of claim 5 wherein the reaction is carried out in dimethyl ether of tetraethylene glycol.

7. The process of claim 1 wherein the concentration of ethylene glycol is between 0.4 and 5 gram moles per liter of reaction mixture.

* * * * *